United States Patent
Jakob et al.

(10) Patent No.: US 6,202,496 B1
(45) Date of Patent: Mar. 20, 2001

(54) APPARATUS FOR THE MEASUREMENT OF VISCOELASTIC CHARACTERISTICS OF BODIES

(75) Inventors: Karlheinz Jakob, Geinhausen; Klaus Unseld, Hanau; Volker Herrmann, Würzburg; Hans-Bernd Fuchs, Alzenau, all of (DE)

(73) Assignee: Dunlop GmbH, Hanau (DE)

( * ) Notice: Subject to any disclaimer, the term of this patent is extended or adjusted under 35 U.S.C. 154(b) by 0 days.

(21) Appl. No.: 09/175,853

(22) Filed: Oct. 20, 1998

Related U.S. Application Data

(63) Continuation of application No. PCT/EP98/01003, filed on Feb. 20, 1998.

(30) Foreign Application Priority Data

Feb. 20, 1997 (DE) .............................................. 197 06 744

(51) Int. Cl.[7] .................................................. G01N 33/00
(52) U.S. Cl. ...................... 73/866; 73/12.12; 73/54.01; 73/54.23; 73/54.36
(58) Field of Search .................................. 73/866, 54.01, 73/54.02, 54.14, 54.23, 54.43, 54.38, 78, 79, 81, 82, 83, 85, 54.36, 12.12; 374/142

(56) References Cited

U.S. PATENT DOCUMENTS

| | | | |
|---|---|---|---|
| 3,934,463 | * 1/1976 | Venderjagt | 73/81 |
| 4,111,039 | * 9/1978 | Yamawaki et al. | 73/81 |
| 4,159,640 | 7/1979 | Leveque et al. | 73/81 |
| 4,331,026 | * 5/1982 | Howard et al. | 73/81 |
| 4,383,450 | * 5/1983 | Pringiers et al. | 73/81 |
| 4,450,713 | 5/1984 | Arimatsu | 73/81 |
| 4,667,519 | 5/1987 | Burg et al. | 73/815 |
| 4,848,141 | 7/1989 | Oliver et al. | 73/81 |
| 4,967,601 | * 11/1990 | Teramoto | 73/789 |

FOREIGN PATENT DOCUMENTS

| | | | |
|---|---|---|---|
| 10 74 882 | 2/1960 | (DE) . | |
| 25 34 207 A1 | 12/1976 | (DE) | G01N/3/32 |
| 28 09 227 A1 | 9/1978 | (DE) | G01N/3/00 |
| 29 39 923 C2 | 4/1981 | (DE) | G01N/3/32 |
| 01 52 194 | 11/1981 | (DE) | G01N/3/32 |
| 32 23 648 C2 | 1/1983 | (DE) | G01N/3/40 |
| 38 18 831 C2 | 12/1989 | (DE) | G01N/3/20 |
| 41 05 115 A1 | 9/1991 | (DE) | G01N/3/40 |
| 40 40 786 A1 | 6/1992 | (DE) | G01N/11/10 |
| 195 16 643 C1 | 8/1996 | (DE) | G01L/1/16 |
| WO 91 16 003 A1 | 10/1991 | (WO) | A61B/10/00 |

OTHER PUBLICATIONS

Translation of German Search Report Dated Jun. 9, 1997, Relating to German Patent Application No. 197 06 744.1.

* cited by examiner

Primary Examiner—Hezron Williams
Assistant Examiner—Thuy Vinh Tran
(74) Attorney, Agent, or Firm—Fitch, Even, Tabin & Flannery

(57) ABSTRACT

A device for measuring the elastic-viscous properties of objects, in particular objects made of an elastomer material such as rubber, has a measurement body movable in relation to a holder and having a measurement head that can be set on a test object, means for moving the measurement body back and forth and means for measuring the path of displacement of the measurement head and/or the force that acts on the measurement head during the reciprocating movement of the measurement body. In order to diversify the possible uses of the device and to simplify the measurement process, the measurement body is mounted in a freely movable housing with a passage for the measurement head and a bearing surface that can be set on the test object.

Figure 1:
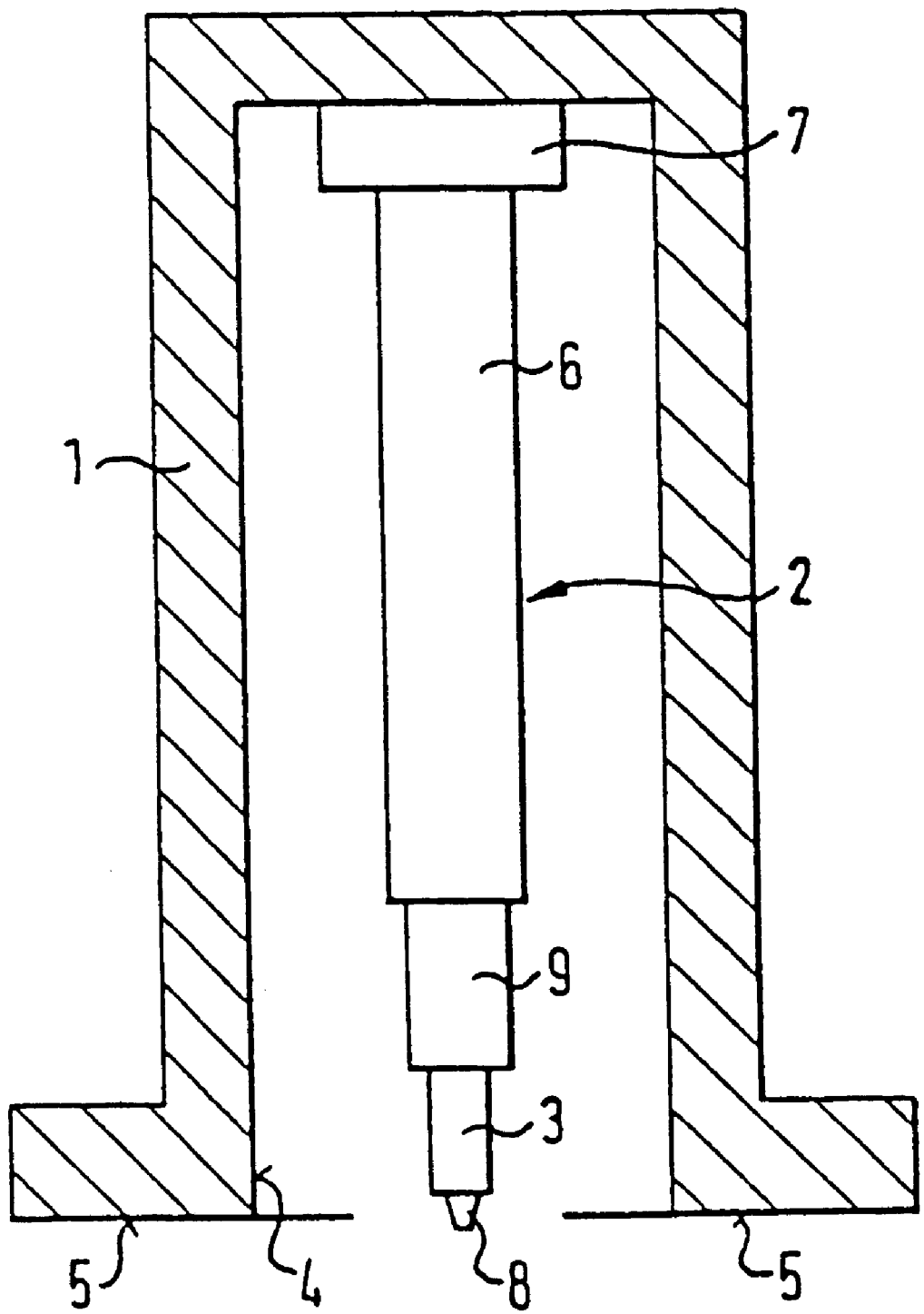

19 Claims, 3 Drawing Sheets

APPARATUS FOR THE MEASUREMENT OF VISCOELASTIC CHARACTERISTICS OF BODIES

This is a continuation, of prior application number PCT/EP98/01003, filed Feb. 20, 1998 and designating the United States of America, which is hereby incorporated herein by reference in its entirety.

The present invention relates to an apparatus for the measurement of viscoelastic characteristics of bodies, in particular of bodies of elastomeric materials such as rubber, comprising a measurement body which is displaceably mounted relative to the holder and which has a measuring head which can be placed onto a sample body and means for the to and fro movement of the measurement body and means for the measurement of the path of displacement of the measurement head and/or of the force acting on the measurement head during the to and fro movement of the measurement body.

An apparatus of this kind is known from DE 40 40 786 A1. In this known apparatus a sample body is laid for the measurement on a measurement table which is provided beneath the holder with the measurement body. The holder must be rigidly supported relative to the measurement table in order to achieve reproducible results during the measurement.

This apparatus admittedly has the advantage, when compared with other apparatuses for the measurement of viscoelastic characteristics, that no special test preparation and in particular no clamping of the sample to a clamping fixture is required. Nevertheless, this apparatus has disadvantages in its utility, because the samples must be arranged on the sample table beneath the measurement head. The arrangement of the sample body on the sample table requires time and is not possible for all sample bodies, in particular when these have no reasonably flat contact surface.

The invention is based on the object of further developing an apparatus of the initially named kind so that these disadvantages do not arise. In particular the possibilities of use should be enlarged and the handling should be simplified.

This object is satisfied in that the measurement body is mounted in a freely movable housing with an opening for the passage of the measurement head and with an abutment surface which can be placed onto the sample body.

In contrast to the known apparatus the sample body is, in accordance with the invention, not brought into a specific position relative to the apparatus, but rather the freely movable housing of the apparatus of the invention is placed onto the sample body for the measurement of the viscoelasticity. The abutment surface thereby ensures that the sample body adopts a defined position relative to the housing with the measurement body. In this way it is possible to dispense with a rigid sample support table opposite the holder for the measurement body and to make measurements directly at the sample. The apparatus of the invention can thus be formed as a hand apparatus which can be used directly on location.

The measurement of viscoelastic characteristics is of particular importance amongst other things for vehicle tires, for example during the testing of new tire mixtures. Hitherto, sample bodies were made of the respective tire material and fixedly clamped into a measuring apparatus in accordance with DIN 53513. The disadvantage of this is that sample bodies must first be manufactured or cut out of an available tire before a measurement can take place. This has, moreover, the disadvantage that a tire is destroyed after the measurement has taken place. Thus, it is not possible to measure one and the same tire after different running periods.

The invention now makes it possible to measure the viscoelasticity of different components of the tire, such as for example the tread and the side wall without destroying the tire. For this purpose the housing with the abutment surface is placed onto a suitable position of the vehicle tire and the measurement is carried out. After the measurement has been completed the tire can be used again, for example in order to make a renewed measurement of the viscoelasticity and also of measurements of another kind after a longer running period. In just the same way it is possible with the hand apparatus of the invention to carry out measurements on a tire mounted on a vehicle. A measurement can thus for example also be carried out directly after a conclusion of a test run on the still hot tire, whereby a much simpler, or a more rapid measurement of the viscoelasticity of a heated tire close to reality is possible than with an independently heated sample body of tire material.

In accordance with a development of the invention means are provided by which it is ensured that the abutment surface of a housing sits firmly on the sample body during a measurement procedure. Through this feature the use of the apparatus of the invention as a hand device is improved, in that the housing with the measurement body is prevented from moving relative to the sample body during the measurement procedure. In this way it is ensured that reproducible results of high quality can be achieved even with a hand device.

One possibility for such means consists in forming the abutment surface as a standing surface of defined size. The housing with the measurement body can then be placed with its standing surface on the sample body, so that firm contact between the abutment surface and the sample body is ensured by the self-weight of the housing. The housing can for example have a weight between ca. 0.5 and 1 kp.

Another possibility consists in providing a pressure sensor which detects a pressing contact of the abutment surface on the sample body. A pressure sensor of this kind can for example be a planar pressure disk clamped between two mutually confronting flat surfaces of two parts of the housing. A valid measurement is only present when the pressure sensor detects a contact pressure above a specific threshold value. The selection of valid measurements can in this arrangement take place either via corresponding automatic means or however simply manually in that a suitable indicator device, for example a lamp, indicates when a sufficient contact pressure of the housing at the sample body is present.

In accordance with a further embodiment of the invention the zero position of the measurement head is determined by a predetermined depth of penetration. Other than in the apparatus known from DE 40 40 786 A1 the zero position is thus not determined via the indentation force of the measurement head into the sample body. This has the advantage, in particular with relatively soft sample bodies, that a penetration of the measurement head which is too deep and thus the danger of destroying the sample body is avoided. This is amongst other things also important because the apparatus of the invention is to be used on a final product on location, and not only on a specially manufactured sample body.

The depth of penetration in the zero position is preferably so selected that the deflection of the measurement head during the measurement lies in a range of at least approximately linear force-displacement ratio. In this way the reliability of the measured value obtained is increased. On measuring a body of elastomeric material the depth of penetration in the zero position amounts for example to ca. 100 to ca. 500 µm, when measuring tire mixtures, in particular to ca. 500 µm. These values can however also be selected differently, particularly in dependence on the shape of the penetration body. It is advantageous to determine suitable values by preliminary tests.

In accordance with a further embodiment of the invention the measurement head projects beyond the abutment surface of the housing in accordance with the desired depth of penetration. By placement of the abutment surface of the housing onto the sample body the penetration of the measurement head into the sample body by the desired amount is thus achieved in a simple manner. Another possibility consists in providing means by which the measurement head can be moved out of the housing into its zero position before the measurement is started. In both cases the zero position of the measurement head is preferably selectable. The zero position can thus be set at the apparatus, in a suitable manner, in particular in dependence on the material of the sample body.

In accordance with a further embodiment of the invention the deflection of the measurement head during the measurement is determined by the path of deflection. Again in contrast to DE 40 40 786 A1 the deflection is not determined by the deflection force. It is also possible in this way to avoid a possibly too heavy loading and thus the danger of a destruction of the sample body.

In just the same way it is also preferred here when the path of deflection is made selectable at the apparatus. The deflection can thereby be suitably selected in dependence on the material of the sample body, on the one hand. On the other hand, the possibility exists of carrying out measurements with different deflection on one and the same sample body and thereby of obtaining additional pronouncements concerning the sample body.

The path of deflection is kept as small as possible in accordance with a further design of the invention. In this way not only is the danger of destruction of the sample body reduced, but rather the quality of the results that are obtained is also improved, because the sample behaves approximately linearly with small deflections. It has been shown that in this way measurement values are obtained which lie very close to customary measurement devices with fixedly clamped sample bodies. The path of deflection for the measurement of a body of elastomeric material amounts for example to ca. 5 to 25 µm, in particular to ca. 5 µm with a sample body of tire material.

In accordance with a further embodiment of the invention the frequency of the to and fro movement of the measurement head is also selectable. In this case the frequency can be varied both in dependence on the material of the sample body and also to achieve additional pronouncements concerning the sample body. With a sample body of elastomeric material the frequency preferably amounts to between ca. 1 and 15 Hz, in particular to ca. 10 Hz. These frequencies have proved to be particularly suitable, in particular for the measurement of sample bodies of tire material. The excitation can take place in particular in accordance with a sine function or with another periodic function, for example a rectangular or triangular function.

In accordance with the further embodiment of the invention means are provided for determining the temperature of the sample body. Temperature sensors which work without contact are particularly suitable in this respect, such as for example infrared sensors. By measuring the temperature of the sample body one can, on the one, hand ensure that the measurement values that are obtained are reproducible and comparable to one another. On the other hand, additional pronouncements concerning the behaviour of the sample body can be obtained hereby, so that for example the viscoelasticity of tire material can be determined at different operating temperatures of a vehicle tire.

A piezoelement, in particular a so-called stacked translator is preferably provided for the movement of the measurement head in the housing. A piezoelement advantageously enables a deflection of the measurement head by low values, such as is desirable to achieve a linear behaviour of the sample body. It is preferred when the piezoelement is arranged with a path measuring device in a regulating circuit. In this way it can be ensured that the deflection path provided for the measurement body is precisely maintained. A further piezoelement or a strain gauge can for example serve as the path measuring device.

In accordance with a further embodiment of the invention the measuring head is formed as a penetration body in accordance with DIN 53505 for the measurement of sample bodies of elastomeric material, in particular as a Shore-A penetration body. Through the use of a DIN penetration body measured values can be obtained with the apparatus of the invention which are directly comparable with DIN measurement values. Since the measured values obtained with the apparatus of the invention have a very high quality it is possible in many cases to dispense with a DIN measurement. Naturally other penetration bodies can however also be used, with suitable measurement conditions, in particular the depth of penetration and also the frequency and others can be found, in each case preferably by preliminary investigations, in particular in dependence on the penetration body and on the material investigated.

The apparatus of the invention can be used in many ways. Thus it can already be used during the development of tire mixtures, and indeed a measurement on still unvulcanised material provides good results. Moreover a measurement on the finished tire and on an installed tire is possible.

An embodiment of the invention is shown in the drawing and will be described in the following. There are shown, in each case in schematic illustration, FIG. 1 a section through the housing with measurement body of an apparatus in accordance with the invention, FIG. 2 a specified illustration of the lower section of the measurement body of the apparatus of FIG. 1, and FIG. 3 a possible overall arrangement of an apparatus in accordance with the invention.

As FIG. 1 shows, a measurement body 2 with a measurement head 3 is arranged in a housing 1. The housing 1 has an opening 4 through which the measurement head 3 of the measurement body 2 projects out of the housing, and also an abutment surface 5 with which the housing 1 can be placed onto a sample body. The abutment surface 5 is, in this arrangement, disposed around the opening 4, so that the outwardly projecting part of the measurement head 3 simultaneously determines the projection "a" of the measurement head 3 beyond the abutment surface 5.

The measurement body 2 includes a piezoelement 6 formed as a stacked translator, which is connected to a force pick-up 7 formed by a quartz crystal which is in turn secured to the housing 1. The measurement head 3 of the measurement body 2 has a tip 8 formed as a Shore-A penetration body in accordance with DIN 53505 and is connected to the lower end of the piezoelement 6 via a connection element 9.

Figure 2:
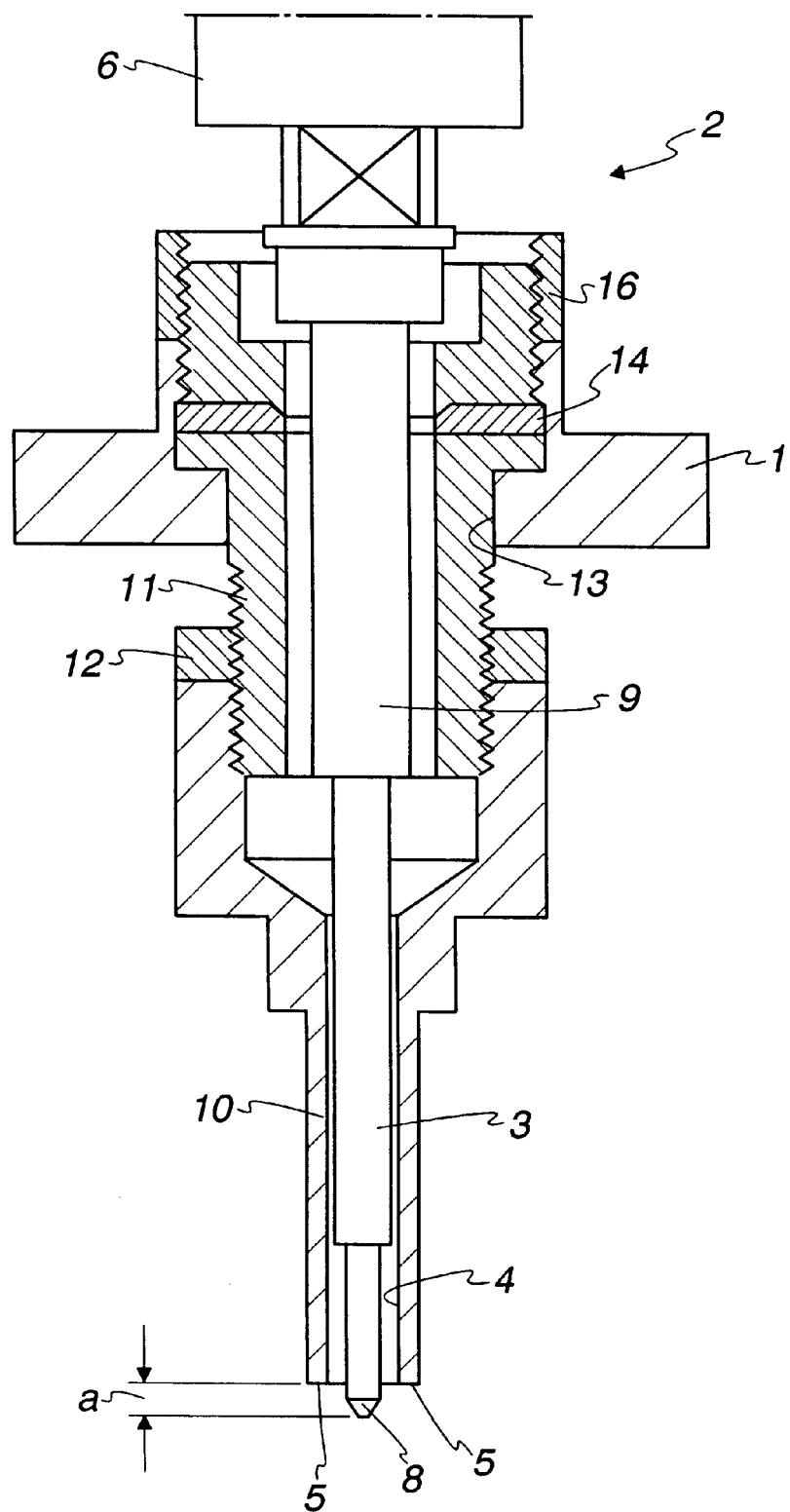

A preferred embodiment of the lower section of the measurement body 2 can be more precisely recognized in FIG. 2. The measurement head 3 is surrounded by an abutment sleeve 10 at the lower end of which the opening 4 and the abutment surface 5 are formed. The abutment sleeve 10 is screwed onto a pressure sleeve 11 and locked by means of a locking nut 12. The pressure sleeve 11 is inserted into a cutout 13 of the housing 1 and fixed there through the intermediary of a planar pressure disk 14 by means of a screwed-in sleeve screwed into the housing 1 and a locking nut 16. The pressure sleeve 11 is thus movable in the recess 13 relative to the pressure disk 14 which is firmly supported at the housing 1 and transfers onto the pressure disk 14 the forces exerted via the abutment surface 5 onto the abutment sleeve 10. Not shown are means for producing a signal in dependence on the size of the pressure exerted on the pressure disk 14.

Figure 3:
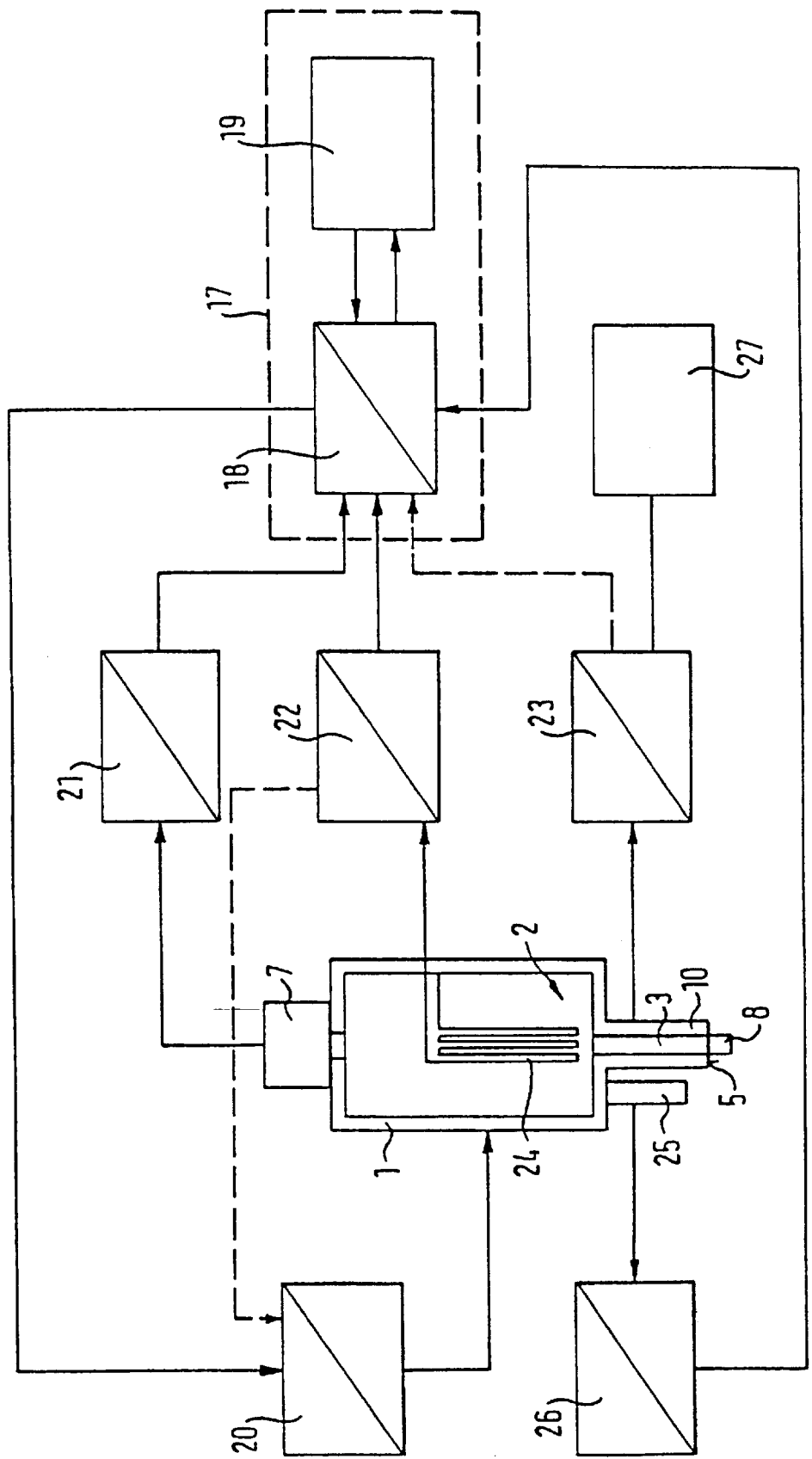

The illustration of principle of a possible overall arrangement of an apparatus in accordance with the invention shown in FIG. 3 includes, in addition to the housing 1 with the measurement body 2, an evaluation and control unit 17, for example a computer 19 equipped with an analog/digital converter 18. The evaluation and control unit 17 is connected via a measurement converter 20 to the measurement body 2. Moreover, the evaluation and control unit 17 receives, in each case via a measurement converter 21, 22, 23, output signals of the force pick-up 7, of a path measurement device 24, which is for example formed as a strain gauge, and of the pressure disk 14. Moreover a temperature measuring device 25, in particular formed as an infrared sensor, is arranged on the housing 1, with the output signals of the temperature measuring device being supplied to a further measurement converter 26. Additionally, or alternatively, the output signals of the temperature measurement device 25 can be supplied, as illustrated, to the evaluation and control unit 17.

For the measurement of the viscoelastic characteristics of a sample body with the apparatus of the invention the housing 1 is placed onto the sample body in such a way that the tip 8 of the measurement head 3 presses into the sample body and the abutment surface 5 of the abutment sleeve 10 sits on the sample body. A determination is made via the pressure disk 14 whether an adequate contact pressure of the contact pressure sleeve 10 on the sample body is present in order to ensure a stable measurement. On exceeding a correspondingly preset threshold value, an output signal of the pressure disk 14 is applied to the indicator 27. In this way an indication is given that an exploitable measurement is possible. In addition, or alternatively, the output signal of the pressure disk 14 can be supplied to the evaluation and control unit 17 in order to enable use of a measurement value that is received only with adequate contact pressure of the contact pressure sleeve 10 on the sample body.

With the housing 1 placed onto the sample body the viscoelastic measurement is carried out in that the evaluation and control unit 17 causes the measurement body 2 to execute oscillations of a desired frequency via the measurement converter 20. The movement of the measurement body 2 is thereby brought about by the piezoelement and detected on the one hand by the force pick-up 7 and on the other hand by the path measurement device 24. At the same time the temperature of the sample body can be determined via the temperature measuring device 25. The measurement signals of the force pick-up 7, of the path measurement device 24 and of the temperature measurement device 25 are supplied via the measurement converter 21, 22 and 26 to the evaluation and control unit 17. The data are supplied to the computer 19 via the analog/digital converter 18 where they are displayed and can be subjected to further processing.

From the data that is received the viscoelasticity of the sample body is determined, for example in accordance with the equation:

$$\sigma(t)=E[\epsilon_m+\epsilon_a\cdot\sin(\omega t)]+\eta\omega\epsilon_a\cdot\cos(\omega t)$$

or the equation:

$$f(t)=S_H[1_o+1_a\cdot\sin(\omega t)]+\eta_H\omega 1_a|\cdot\cos(\omega t),$$

in particular as the real and imaginary part of the stiffness $S_H$ as a parameter related to the modulus of elasticity. In this respect $\sigma(t)$ course of the stress over time in MPa
    E modulus of elasticity in MPa
    $\eta$ viscosity in MPa·s
    $\epsilon_m$ static elongation in %
    $\epsilon_a$ elongation amplitude in %
    $\omega$ circular frequency in Hz
    f(t) course of the force over time in N
    $S_H$ stiffness in N/m
    $\eta_H$ a parameter related to the viscosity in N·s/m
    $1_o$ static deflection in mm
    $1_a$ dynamic deflection in mm The stiffness can be determined both via the measured force and also via the measured path in dependence on the force applied or better in dependence on the path of the measurement body. Through this double determination the quality of the measurement result can be further improved.

The reproducibility of the values obtained is additionally ensured in that as a result of the tuning of the apparatus, in particular high stiffness and low moved mass through the piezo construction, the measurements take place far below the natural resonant frequency of the apparatus.

What is claimed is:

1. Apparatus for the measurement of viscoelastic characteristics of sample bodies, in particular of sample bodies of elastomeric materials, comprising a measurement body, which has a measuring head for placement onto a sample body and is displaceably mounted in a freely movable housing having an opening for the passage of the measuring head and an abutment surface for placement onto the sample body, a piezoelement for producing to and fro movement of the measurement body and apparatus for measurement of a path of displacement of the measurement head and/or of the force acting on the measurement head during the to and fro movement of the measurement body, the measurement head being formed as a penetration body which in the zero position projects beyond the abutment surface of the housing in accordance with a desired depth of penetration.

2. Apparatus in accordance with claim 1, wherein the penetration body is formed in accordance with Deutsche Industrie Norm 53505 for the measurement of test bodies of elastomeric material.

3. Apparatus in accordance with claim 1, wherein the depth of penetration in the zero position is selected so that displacement of the penetration body lies in a region of approximately linear force-displacement ratio.

4. Apparatus in accordance with claim 3 wherein the depth of penetration in the zero position for the measurement of a body of elastomeric material amounts to ca. 100 to 500 $\mu$m.

5. Apparatus in accordance with claim 3, wherein the displacement of the penetration body is selected to be so small that the sample body behaves approximately linearly.

6. Apparatus in accordance with claim 5 wherein the displacement of the penetration body amounts to ca. 5 to ca. 25 $\mu$m of the measurement of the body of elastomeric material.

7. Apparatus in accordance with claim 1, wherein the displacement of the penetration body during the measurement is determined via the path of deflection.

8. Apparatus in accordance with claim 7 wherein the piezoelement is arranged in a regulating circuit with a displacement measuring device.

9. Apparatus in accordance with claim 1, wherein the frequency of the to and fro movement of the measurement head is selectable.

10. Apparatus in accordance with claim 9, wherein the frequency of the to and fro movement of the measurement head amounts to ca. 1 Hz to ca. 15 Hz.

11. Apparatus in accordance with claim 1, comprising apparatus for determining the temperature of the sample body.

12. Apparatus in accordance with claim 1, comprising apparatus for ensuring that the abutment surface sits firmly on the sample body during a measurement procedure.

13. Apparatus in accordance with claim 12, wherein the abutment surface is formed as a standing surface of defined size.

14. Apparatus in accordance with claim 1, comprising a pressure sensor for detecting a pressing contact of the abutment surface at the sample body.

15. Apparatus in accordance with claim 14, comprising a planar pressure disk clamped between two confronting flat surfaces of two parts of the housing.

16. Apparatus in accordance with claim 1, comprising indicator means for indicating a detected contact of the abutment surface on the sample body.

17. Apparatus in accordance with claim 16, comprising means for causing a measurement to be carried out or used only when contact of the abutment surface on the sample body is detected.

18. Apparatus in accordance with claim 2, wherein the penetration body is a Shore-A penetration body.

19. Apparatus in accordance with claim 10, wherein the frequency of the to and fro movement of the measurement head is ca. 10 Hz.

* * * * *